US012708692B2

(12) United States Patent
Ng et al.

(10) Patent No.: US 12,708,692 B2
(45) Date of Patent: Aug. 18, 2026

(54) VOLATILE COMPOSITION DISPENSER WITH IMPROVED SCENT INTENSITY CONTROL

(71) Applicant: The Procter & Gamble Company, Cincinnati, OH (US)

(72) Inventors: Desmond Ng, Singpore (SG); Rahul Vyas, Singapore (SG); Mei San Gigi Cho, Singapore (SG); Stefano Deflorian, Trento (IT); Walter Sordo, Trento (IT)

(73) Assignee: The Procter & Gamble Company, Cincinnati, OH (US)

(*) Notice: Subject to any disclaimer, the term of this patent is extended or adjusted under 35 U.S.C. 154(b) by 156 days.

(21) Appl. No.: 18/648,611

(22) Filed: Apr. 29, 2024

(65) Prior Publication Data

US 2024/0358877 A1 Oct. 31, 2024

Related U.S. Application Data

(60) Provisional application No. 63/462,250, filed on Apr. 27, 2023.

(51) Int. Cl.
*A61L 9/12* (2006.01)
*B60H 3/00* (2006.01)

(52) U.S. Cl.
CPC ........... *A61L 9/12* (2013.01); *A61L 2209/131* (2013.01); *A61L 2209/134* (2013.01); *A61L 2209/15* (2013.01); *B60H 3/0035* (2013.01)

(58) Field of Classification Search
CPC ................. A01M 1/2027; A01M 29/12; A61L 2209/131; A61L 2209/133;
(Continued)

(56) References Cited

U.S. PATENT DOCUMENTS 8,485,454 B1 * 7/2013 Irvin ....................... A61L 9/125
239/34
9,192,690 B2 11/2015 Zobele
(Continued)

FOREIGN PATENT DOCUMENTS

CN 215793089 U 2/2022
CN 216022302 U 3/2022
(Continued)

OTHER PUBLICATIONS

PCT Search Report and Written Opinion for PCT/US2024/025648 dated Aug. 23, 2024; 13 pages.

*Primary Examiner* — Scott J Walthour
(74) *Attorney, Agent, or Firm* — Elizabeth A. Conklin; Carolyn S. Powell

(57) ABSTRACT

A volatile composition dispenser includes a cartridge comprising a reservoir of at least one liquid volatile composition and a breathable membrane for enclosing the reservoir and evaporating the at least one liquid volatile composition into the atmosphere upon activation of the volatile composition dispenser. The cartridge is disposed in a housing having opposing first and second walls, while the second wall has a plurality of evaporation vents and is characterized by a Total Vent Area (T). A scent intensity controller is attached to said housing for adjustably covering at least some or portions of said plurality of evaporation vents on the second wall. The volatile composition dispenser is characterized by an Un-Adjustable Vent Area (U) that is no more than 15% of the Total Vent Area (T), which helps to deliver improved scent intensity control.

11 Claims, 12 Drawing Sheets

(58) Field of Classification Search
CPC .. A61L 2209/134; A61L 2209/15; A61L 9/12; B60H 3/0007; B60H 3/0028; B60H 3/0035; B60H 3/0085; B60H 2003/0042
See application file for complete search history.

(56) References Cited

U.S. PATENT DOCUMENTS

| | | | | |
|---|---|---|---|---|
| 10,143,766 | B2 | 12/2018 | Gruenbacher | |
| 10,173,607 | B1 * | 1/2019 | Omelchenko | B60H 3/0028 |
| 2017/0319733 | A1 * | 11/2017 | Hu | A61L 9/12 |
| 2020/0360557 | A1 * | 11/2020 | Wu | A61L 9/12 |

FOREIGN PATENT DOCUMENTS

| | | | |
|---|---|---|---|
| CN | 216424031 | U | 5/2022 |
| EP | 2832375 | A1 | 2/2015 |
| EP | 3202426 | A2 | 8/2017 |
| EP | 3682910 | B1 | 9/2021 |
| TW | M577739 | U | 5/2019 |
| WO | 2017131942 | A2 | 8/2017 |
| WO | 2017192640 | A1 | 11/2017 |

* cited by examiner 136
130
120
134
132
126c
126b
126a 136
130
120
132
134
122
126c
126b
126a 130
136
132
120
134
122
126c
126b
126a

VOLATILE COMPOSITION DISPENSER WITH IMPROVED SCENT INTENSITY CONTROL

TECHNICAL FIELD

The present disclosure relates to devices for dispensing a volatile composition, and more particularly a non-energized and continuous volatile composition dispenser with an improved intensity control mechanism, as well as methods of using same to adjust intensity of scent delivered thereby.

BACKGROUND

A volatile composition dispenser can be used to evaporate a volatile composition into an atmosphere, such as a domestic atmosphere or a vehicle passenger compartment atmosphere, for example, in order to deliver a variety of benefits, such as air freshening or perfuming of the atmosphere. Non-energized dispensing systems, for example, systems that are not powered by electrical energy, are a popular way for delivery of the volatile composition into the atmosphere. These dispensing systems can be classified into those that may require human actuation, such as aerosols, and those that may not require human actuation, such as wick-based systems and gels. The first type of dispensing system delivers the volatile composition on demand, while the second type of dispensing system delivers the volatile composition in a more continuous manner.

There are volatile composition dispensers with built-in features for adjusting the intensity of fragrance or scent delivered thereby. For example, U.S. Pat. No. 10,143,766 discloses a volatile composition dispenser with an air flow adjustment member (see FIG. 15 of U.S. Pat. No. 10,143,766) or an intensity dial element (see FIG. 19 of U.S. Pat. No. 10,143,766) that allows the consumer to adjust the air flow rate through the volatile composition dispenser and thereby adjusting the amount of volatile composition dispensed by such volatile composition dispenser into a surrounding atmosphere. However, despite the design intent to provide consumer-noticeable scent intensity difference at different settings (i.e., low and high scent intensity settings), little or no difference is observed for perfume evaporation between the lowest and highest settings at the start of product usage when the scent is the most intense, and toward the end of product life when the scent is the least intense, perfume evaporation at the lowest setting is still about 90% of that at the highest setting. This small difference in perfume evaporation provides no meaningful differentiation of scent intensity delivered at the lowest and highest settings.

There is therefor a need to provide volatile composition dispensers with improved scent intensity control mechanism, especially for delivery meaningful and consumer-noticeable scent intensity differentiation at different scent intensity settings.

SUMMARY

The present disclosure provides a volatile composition dispenser, comprising:

(a) a cartridge comprising a reservoir of at least one liquid volatile composition and a breathable membrane for enclosing said reservoir and evaporating said at least one liquid volatile composition into the atmosphere upon activation of said air freshener, wherein said breathable membrane defines an Evaporative Surface Area (E);

(b) a housing having opposing first and second walls that are joined along their peripheries with each other to define an internal compartment in which the cartridge is disposed, wherein a gap exists between said breathable membrane of the cartridge and the second wall of the housing, wherein said gap has a width ranging from about 1 mm to about 10 mm, optionally from about 1 mm to about 5 mm, or from about 1 mm to about 3 mm, or from about 1 mm to about 2 mm, wherein said second wall has a plurality of evaporation vents that enable fluid communication between the internal compartment and the exterior of said housing, wherein said first wall is free of any evaporation vent, and wherein said second wall is characterized by a Total Vent Area (T) ranging from 5% to 85%, optionally from about 10% to about 70%, or from about 15% to about 60%, or from about 20% to about 50%, of the Evaporative Surface Area (E); and (c) a scent intensity controller attached to said housing for adjustably covering at least some or portions of said plurality of evaporation vents on the second wall, wherein those evaporation vents or portions thereof that cannot be adjustably covered by the scent intensity controller define an Un-Adjustable Vent Area (U), and wherein the Un-Adjustable Vent Area (U) is no more than 15%, optionally from 0% to about 12%, or from 0% to about 10%, or from 0% to about 5%, or from 0 to about 3%, of the Total Vent Area (T).

Specifically, the scent intensity controller is movable between two or more different scent intensity positions to adjust the intensity of scent released by the volatile composition dispenser, while the volatile composition dispenser further comprises a locking mechanism for locking the scent intensity controller at different scent intensity positions.

In a particular embodiment of the present disclosure, the volatile composition dispenser further comprises a mounting clip connected to the housing for releasably attaching the volatile composition dispenser to an air vent (e.g., of an AC unit in a car, home, or office). More specifically, the mounting clip comprises four prongs that define two perpendicularly intersecting gaps for releasably attaching said volatile composition dispenser to the air vent along a first direction and a second direction that is substantially perpendicular to said first direction. Each of such four prongs can be characterized by a length from 10 mm to 40 mm, or from 12 mm to 30 mm, or from 14 mm to 25 mm, or from 16 mm to 20 mm. The two perpendicularly intersecting gaps may have substantially the same widths, which optionally ranges from 0.5 mm to 8 mm, or from 2 mm to 6 mm, or from 3 mm to 5 mm. Alternatively, the two perpendicularly intersecting gaps may have different widths, one of which may range from 0.5 mm to 8 mm, or from 2 mm to 6 mm, or from 3 mm to 5 mm; and the other of which may range from 1 mm to 10 mm, or from 2 mm to 8 mm, or from 4 mm to 7 mm.

The volatile composition dispenser of the present disclosure may further comprise one or more evaporation control elements for reducing the Un-Adjustable Vent Area (U) by blocking one or more un-adjustable openings on said second wall of the housing and preventing fluid communication between the internal compartment and the exterior of said housing through said un-adjustable openings.

The present disclosure also related to a method of varying scent intensity in an interior space, comprising the steps of:

(i) providing a volatile composition dispenser according to any one of the preceding claims in an interior space; and (ii) using the scent intensity controller to adjust the intensity of scent released by said volatile composition.

BRIEF DESCRIPTION OF THE DRAWINGS

The above-mentioned and other features and advantages of the present disclosure, and the manner of attaining them, will become more apparent and the disclosure itself will be better understood by reference to the following description of embodiments taken in conjunction with the accompanying drawings, wherein.

DETAILED DESCRIPTION

Various embodiments will now be described to provide an overall understanding of the principles of the structure, function, manufacture, and use of the apparatuses and methods disclosed herein. One or more examples of these embodiments are illustrated in the accompanying drawings. Those of ordinary skill in the art will understand that the apparatuses and methods specifically described herein and illustrated in the accompanying drawings are non-limiting example embodiments and that the scope of the various embodiments of the present disclosure is defined solely by the claims. The features illustrated or described in connection with one exemplary embodiment may be combined with the features of other exemplary embodiments. Such modifications and variations are intended to be included within the scope of the present disclosure.

Figure 1:
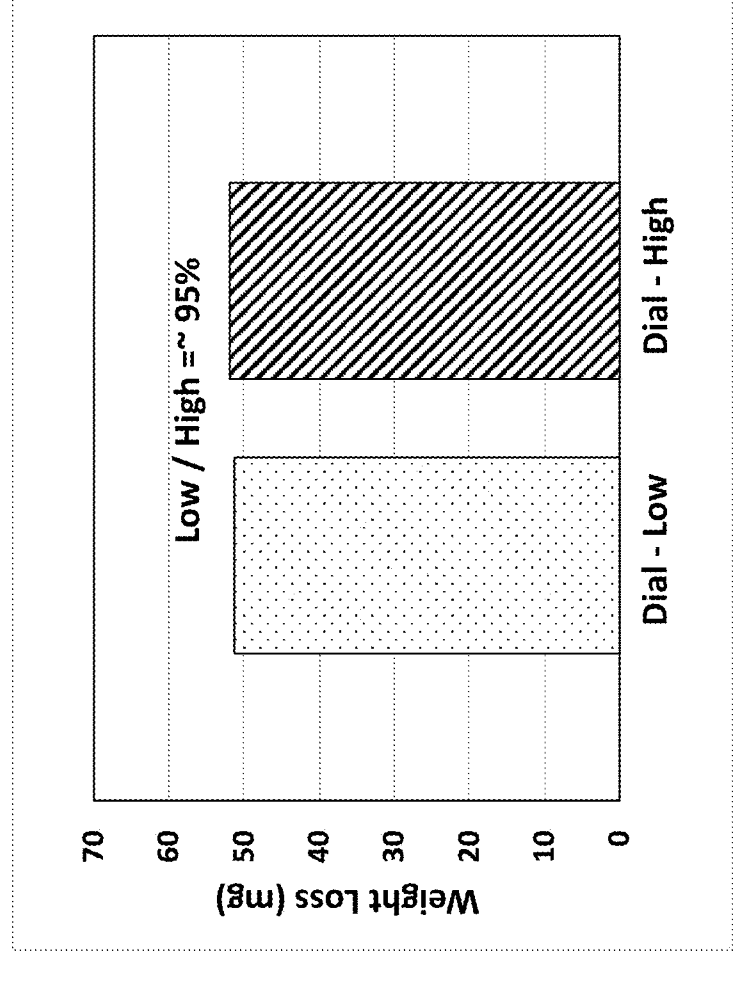
FIG. 1 is a graph showing the comparative perfume weight loss of a prior art volatile composition dispenser at the low scent intensity setting and at the high scent intensity setting, as disclosed by FIG. 19 of U.S. Pat. No. 10,143,766.

FIG. 1 is a graph showing the comparative perfume weight loss of a prior art volatile composition dispenser (as disclosed by FIG. 19 of U.S. Pat. No. 10,143,766) at the low scent intensity setting and at the high scent intensity setting, measured by the method disclosed in Test 1 hereinafter. It is disappointing to see that despite the presence of a scent intensity dial that intends to allow the consumer to adjust the air flow rate through the air freshener and thereby adjusting the amount of perfumes dispensed by such air freshener, the perfume weight loss, which is indicative of the amount of perfumes dispensed by such air freshener, at the low scent intensity setting is about 95% of such at the high scent intensity setting. The 5% difference in perfume weight loss may not be noticeable by consumers. In other words, the prior air freshener delivers little or no consumer-noticeable difference in scent intensity between the low and high scent intensity settings.

It has been a surprising and unexpected discovery of the present disclosure that the existence of small gaps or openings in such prior art air freshener, which cannot be adjustably opened or closed by the scent intensity dial, are responsible for the lack of meaningful differentiation of scent intensity at different intensity settings observed. Although such un-adjustable gaps or openings only count for a small portion of the total opening surface area (e.g., less than 20%), they can allow a disproportional amount of air flow through, which leads to the lack of scent intensity differentiation at the low and high settings.

Figure 2B:
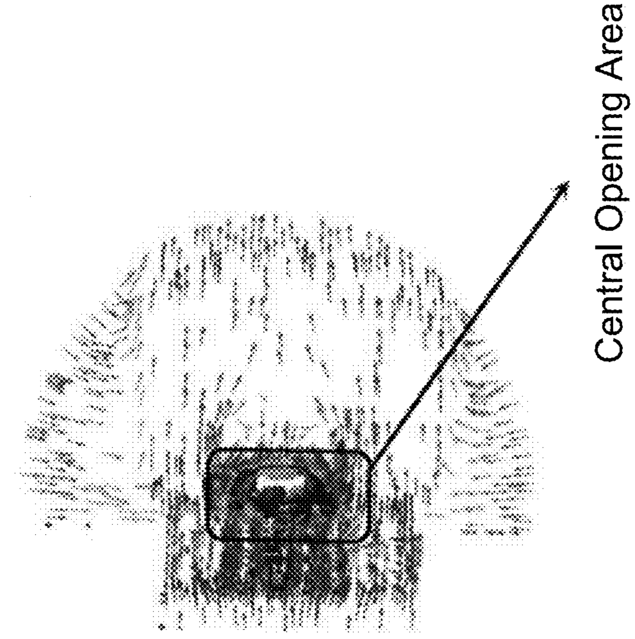
FIG. 2B is a side image modeling air flow paths through the same prior art volatile composition dispenser of FIGS. 1 and 2A.
Figure 2A:
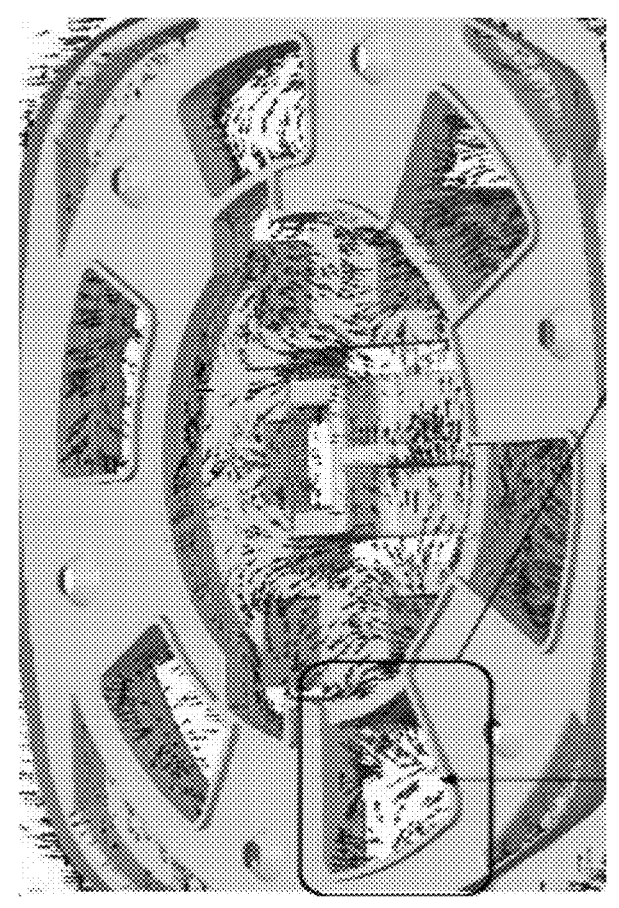
FIG. 2A is a perspective image modeling air flow paths through various evaporation vents on the back wall of the prior art volatile composition dispenser of FIG. 1.

FIG. 2A is a perspective image generated by modeling, which shows air flow paths through various evaporation vents on the back wall of the prior art volatile composition dispenser as shown in FIG. 19 of U.S. Pat. No. 10,143,766. The small arrows are indicative of air flowing through the back wall of the prior art dispenser. As shown in FIG. 2A, the air flows not only through evaporation apertures along peripherals of such dispenser (which can be closed and opened by an intensity dial element), but also through the central openings in the middle (which cannot be closed and opened by the intensity dial element). FIG. 2B is a side image also generated by modeling, showing air flow paths through the same prior art volatile composition dispenser of FIG. 2A. at its lowest setting of scent intensity. Despite the lowest scent intensity setting, a significant amount of air still flows through the prior art dispenser, especially through the un-adjustable central openings. FIG. 2B specifically shows that air flows through the un-adjustable central openings at a velocity much higher than that through the adjustable peripheral evaporation apertures, which are closed at the lowest scent intensity setting. Correspondingly, little or no difference in scent intensity is observed between the lowest and highest intensity settings.

Therefore, the present disclosure provides a volatile composition dispenser with improved intensity control function, by reducing the areas of such un-adjustable central openings and other gaps/openings that may allow un-adjustable air flow through the volatile composition dispenser at the lowest scent intensity setting. Specifically, the volatile composition dispenser of the present disclosure is characterized by an Un-Adjustable Vent Area (U) that is no more than 15%, optionally from 0% to about 12%, or from 0% to about 10%, or from 0% to about 5%, or from 0 to about 3%, of its Total Vent Area (T), as explained in detail hereinafter. Further, it is desirable that such dispenser is capable of dispensing at least one volatile composition at a first Evaporation Rate (E1) at a low scent intensity setting and a second Evaporation Rate (E2) at a high scent intensity setting, wherein E1 is less than 70% of E2, preferably less than 60% of E2, more preferably less than 55% of E2, which may result in a consumer-noticeable scent intensity difference between the low and high settings.

Such parameter(s) help to ensure that consumers have improved control over the amount of scent delivered in their cars, homes, offices, or other enclosed interior spaces. Further, they may increase longevity of the product life, provide consumers with freedom to use seasonal perfumes with a specific intensity setting appropriate for the season, and support development of regional/seasonal usage instructions to achieve consistent scent intensity throughout the product life (e.g., starting on the low scent intensity setting for 5 days, followed by 15 days on the medium scent intensity setting, and ending with 20 days on the high scent intensity setting, so as to deliver consistent scent intensity in Japan for the summer season).

Figure 3B:
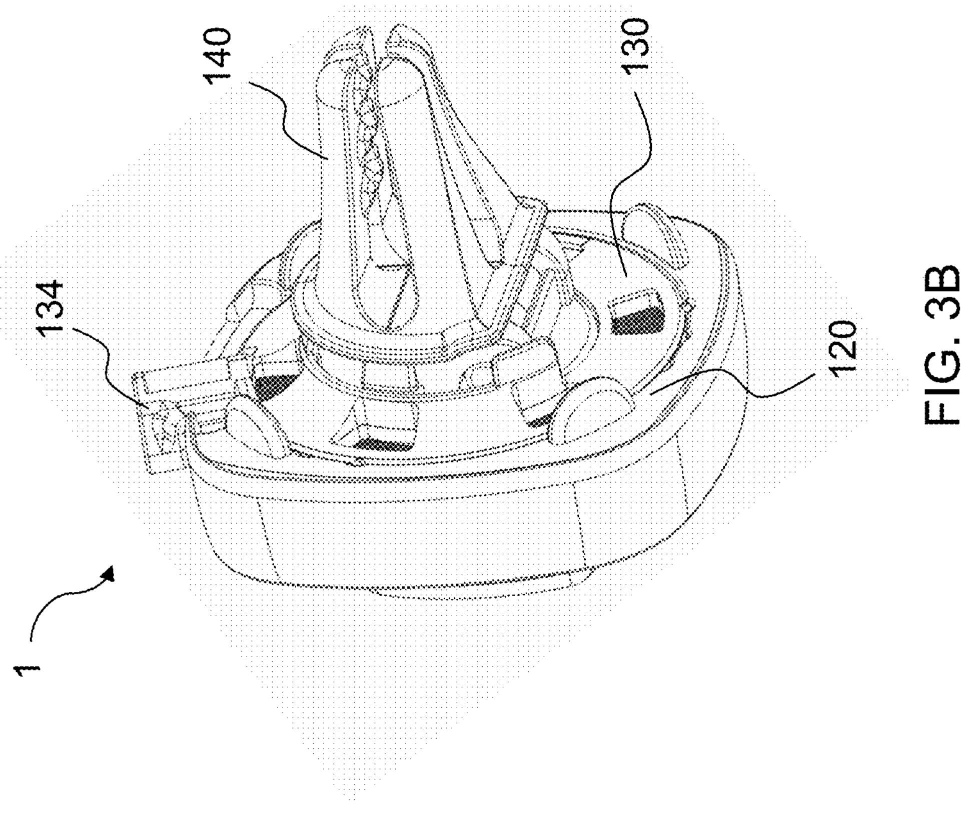
FIGS. 3A-3B are the perspective views of a volatile composition dispenser, in accordance with one non-limiting embodiment of the present disclosure.
Figure 3A:
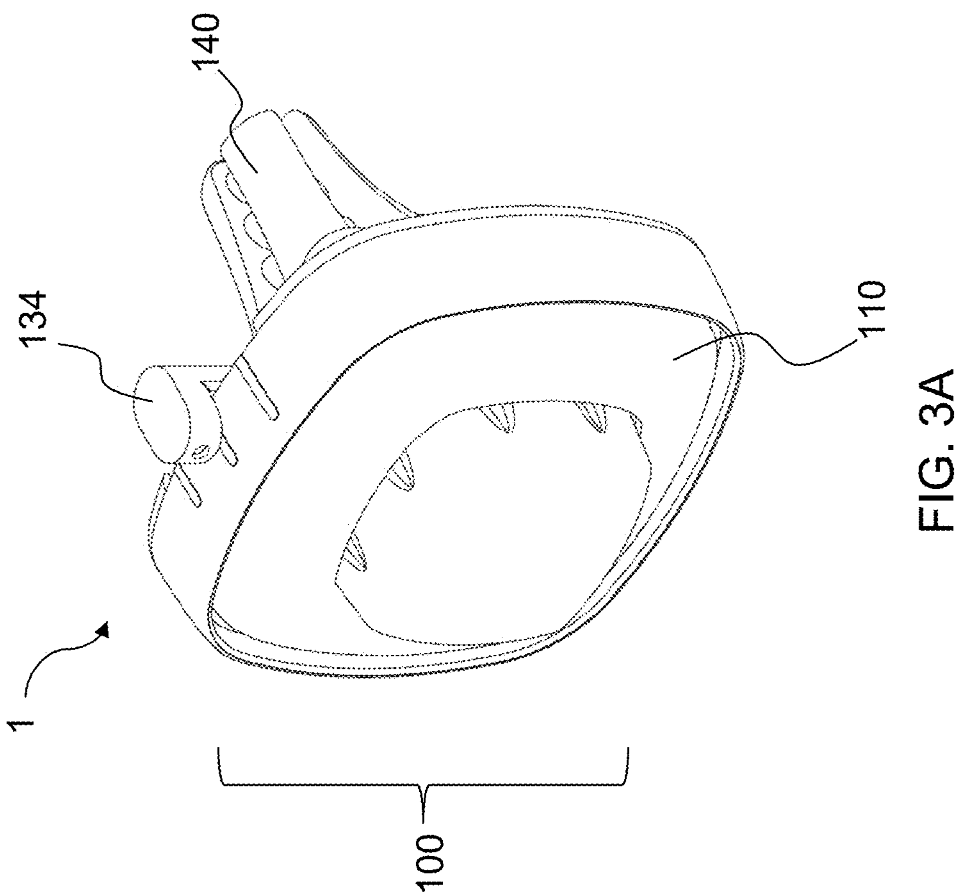
Figure 4:
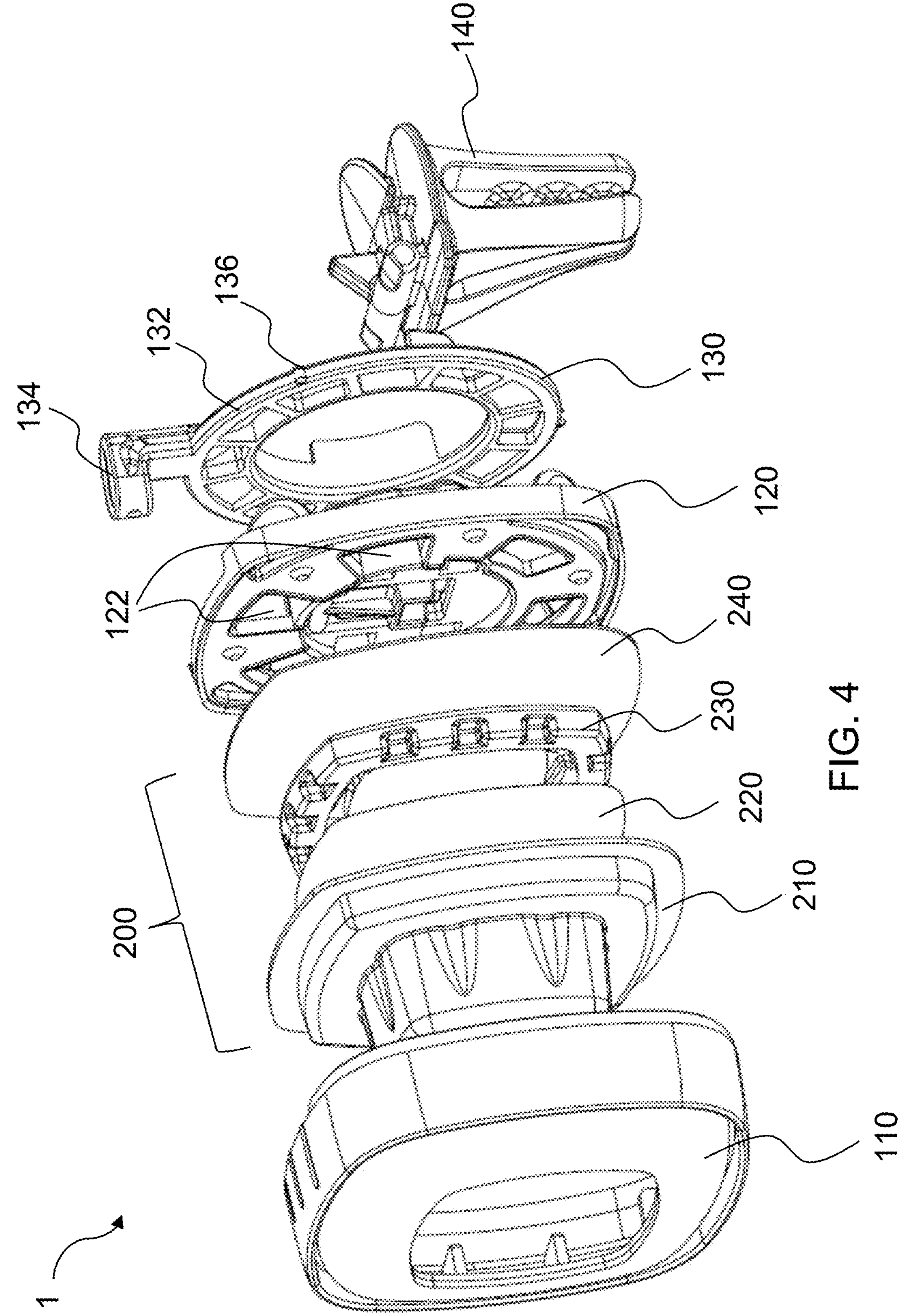
FIG. 4 is an exploded perspective view of various components of the volatile composition dispenser of FIGS. 3A-3B.

FIGS. 3A-3B show perspective views of an exemplary volatile composition dispenser 1, while FIG. 4 shows an exploded perspective view of various components of such volatile composition dispenser 1, in accordance with one non-limiting embodiment of the present disclosure.

Specifically, the exemplary volatile composition dispenser 1 comprises a housing 100 with opposing first and second walls 110 and 120 that are joined along their peripheries with each other to define an internal compartment (not shown). Optionally, the first and second walls 110 and 120 are pivotably or rotatably attached together and can be separated easily by a pivotal or rotational movement.

The first wall 110 is free of any evaporation vents, while the opposing second wall 120 has a plurality of evaporation vents 122 (see FIG. 4) that enable fluid communication between said internal compartment and the exterior of said housing 100.

A cartridge 200 can be disposed in said internal compartment between the first wall 110 and the opposing second wall 120 (see FIG. 4). The cartridge 200 comprises a volatile composition container 210 that defines a reservoir of at least one liquid volatile composition (not shown) and a breathable membrane 240 for enclosing said reservoir and for evaporating said at least one liquid volatile composition into the atmosphere upon activation of the volatile composition dispenser 1. Specifically, a gap exists between said breathable membrane 240 of the cartridge and the second wall 120 of the housing 100, while said gap has a width ranging from 1 mm to 10 mm, optionally from 1 mm to 5 mm, or from 1 mm to 3 mm, or from 1 mm to 2 mm. The closer the gap, the better the control of defined air flow path, which results in better control of the evaporation rate.

Specifically and optionally, the cartridge 200 (as shown in FIG. 4) may further comprise: (1) a rupturable seal 220 configured to cover a portion of the container 210 and to keep said at least one liquid volatile composition within the container 210 until activation occurs; and (2) a rupture element 230 that can be moved, or having at least a portion that can be moved, upon activation of the volatile composition dispenser 1, to puncture the rupturable seal 220 and release at least a portion of said liquid volatile composition from the volatile composition container 210 onto the breathable membrane 240 for evaporation.

On one hand, the breathable membrane 240 defines an Evaporative Surface Area (E). On the other hand, the second wall 120 is characterized by a Total Vent Area (T), which is calculated as the area sum of all evaporation vents 122, as well as any central/peripheral openings or gaps on the second wall 120 that may allow air to flow through. It is desirable that the Total Vent Area (T) is from 5% to 85% of the Evaporative Surface Area (E). Specifically but optionally, the Total Vent Area (T) ranges from about 10% to about 70%, or from about 15% to about 60%, or from about 20% to about 50%, of the Evaporative Surface Area (E). Alternatively, the Total Vent Area (T) may range from 40%, 45%, 50%, 55%, 60%, or even 65% to about 70%, 75%, 80%, 85% or even 90% of the Evaporative Surface Area (E). The higher the percentage of T/E, the better the utilization of the evaporative surface area, which in turn allows higher evaporation that may be needed in certain conditions.

The exemplary volatile composition dispenser 1 further comprises a scent intensity controller 130 attached to said housing 100 (and specifically the second wall 120) for adjustably covering at least some or portions of said plurality of evaporation vents 122 on the second wall 120. Specifically but optionally, the scent intensity controller 130 comprises a rotatable body 132 that fits into a track 124 on the second wall 120 (not visible in FIG. 4 but visible in FIG. 9A), while said rotatable body 132 contains multiple slots or openings that match the evaporation vents 122 on the second wall 120. The scent intensity controller 130 further comprises a protruding scent intensity dial 134 that can be moved by a consumer to rotate the body 132, so as to open or close (or partially open/close) the evaporation vents 122 on the second wall 120.

Specifically, the evaporation vents 122, which can be adjustably opened or closed (or partially opened/closed) by the scent intensity controller 130, define an Adjustable Vent Area (A), while any other central/peripheral openings or gaps on the second wall 120 that may allow air to flow through, but cannot be adjustably opened or closed by the scent intensity controller 130, define an Un-Adjustable Vent Area (U). It is important and critical for the present disclosure that the Un-Adjustable Vent Area (U) is no more than 15% of the Total Vent Area (T). Preferably, the Un-Adjustable Vent Area (U) is from 0% to 12%, or from 0% to 10%, or from 0% to 5%, or from 0 to 3% of the Total Vent Area (T).

Figure 5:
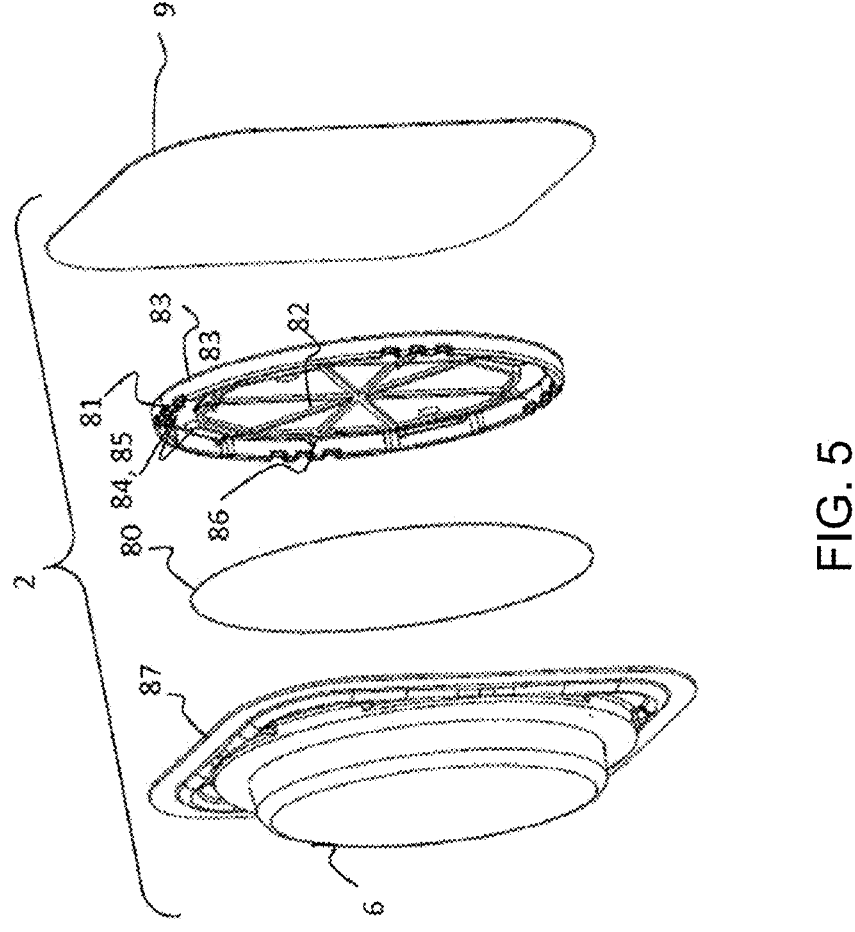
FIG. 5 is an exploded perspective view of various components of a cartridge for a volatile composition dispenser, in accordance with one non-limiting embodiment of the present disclosure.

FIG. 5 is an exploded perspective view of various components of a cartridge 2 for a volatile composition dispenser, in accordance with one non-limiting embodiment of the present disclosure. The volatile composition container 6 defines a reservoir of at least one liquid volatile composition (not shown), with a rupturable substrate 80 sealably attached to and covering the reservoir to prevent said at least one liquid volatile composition from being released until the volatile composition dispenser is activated. The rupturable substrate 80 may be ruptured to release the at least one liquid volatile composition by actuating a rupture element 81 positioned adjacent to the rupturable substrate 80. The rupture element 81 comprises a movable member 82 movably attached to an outer frame 83 by a resilient member 84. The resilient member 84 may be formed of one or more springs 85. One or more rupture members 86 are arranged within the rupture element 81 to puncture holes in the rupturable substrate 80. The rupture members 86 may be pins, needles, teeth, protrusions, and the like. A breathable membrane 9 may be sealably attached to a flange 87 located at the periphery of the container 6. The breathable membrane 9 encloses the container 6 including the reservoir of said at least one liquid volatile composition (not shown), the rupturable substrate 80, and the rupture element 81. The breathable membrane 9 may be configured to flex when a pressure or an actuation force is applied on the breathable membrane 9, for example, by an actuator (not shown) that is configured to move the rupture members 86 toward the rupturable substrate 80 to puncture holes in said substrate 80 and release at least a portion of the liquid volatile composition from the volatile composition container 6 to the breathable membrane 9 for evaporation into the surrounding environment.

Figures 6A, 6B, 6C:
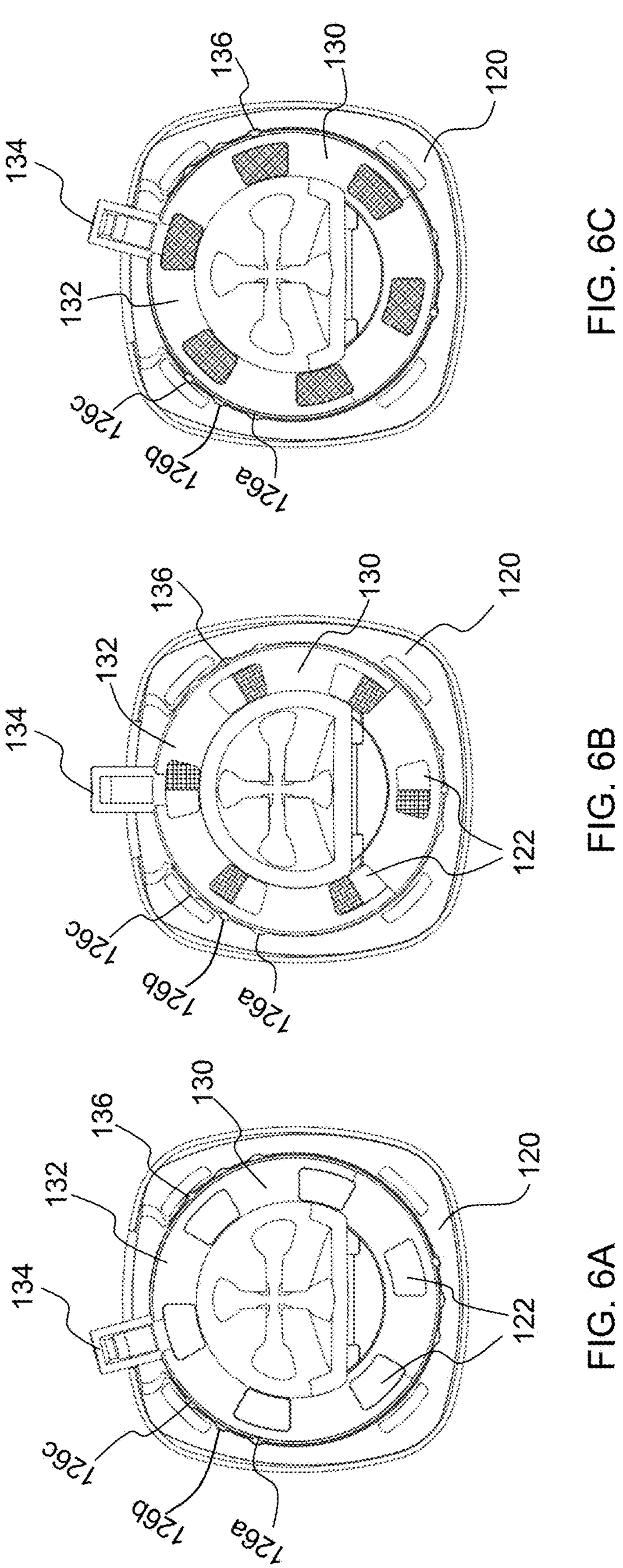
FIGS. 6A-6C are rear views of the volatile composition dispenser of FIGS. 3A and 3B and FIG. 4, with the scent intensity controller moving between three different scent intensity positions to adjust the intensity of scent released by the volatile composition dispenser, in accordance with one non-limiting embodiment of the present disclosure.

FIGS. 6A-6C are rear views of the volatile composition dispenser 1 of FIGS. 3A and 3B and FIG. 4, with the scent intensity controller 130 moving between three different scent intensity positions to adjust the intensity of scent released by the volatile composition dispenser 1, in accordance with one non-limiting embodiment of the present disclosure. Specifically, FIG. 6A shows the scent intensity controller 130 placed at the highest scent intensity setting, with the protruding scent intensity dial 134 moved to the left side and the slots or openings on the rotatable body 132 fully aligned with the evaporation vents 122 on the second wall 120. At this setting, air can flow freely through the evaporation vents 122 to release the liquid volatile composition from the volatile composition dispenser 1 into the surrounding environment. FIG. 6B shows the scent intensity controller 130 placed at a medium scent intensity setting, with the protruding scent intensity dial 134 moved to the middle. The slots or openings on the rotatable body 132 are only partially aligned with the evaporation vents 122 on the second wall 120, while partially obstructed by the non-opening parts of the second wall 120 (marked by the cross-hatching). At this setting, air flow through the evaporation vents 122 is partially restricted, and only a limited amount of the liquid volatile composition can be released from the volatile composition dispenser 1 into the surrounding environment. FIG. 6C shows the scent intensity controller 130 placed at the lowest scent intensity setting, with the protruding scent intensity dial 134 moved to the right. The slots or openings on the rotatable body 132 are now fully offset from the evaporation vents (not visible any more) on the second wall 120, i.e., they are fully obstructed by the non-opening parts of the second wall 120 (marked by the cross-hatching). At this setting, air flow through the evaporation vents 122 is completely blocked, and little or no liquid volatile composition can be released from the volatile composition dispenser 1 into the surrounding environment through such evaporation vents 122.

Optionally, the volatile composition dispenser 1 of the present disclosure comprises a locking mechanism for locking the scent intensity controller 130 at different scent intensity positions. Such a locking mechanism functions to stabilize the scent intensity controller 130 at a desired or specifically selected scent intensity position and avoid inadvertent movement or switch thereof to a different scent intensity position, especially due to gravity (e.g., when the volatile composition dispenser 1 is rotated in such a way that the scent intensity dial 134 is no longer position on top but is either on the left side or the right side, or when the volatile composition dispenser 1 is used for delivering scent to an interior space that is subject to significant movements or vibrations, such as a vehicle).

Figure 9B:
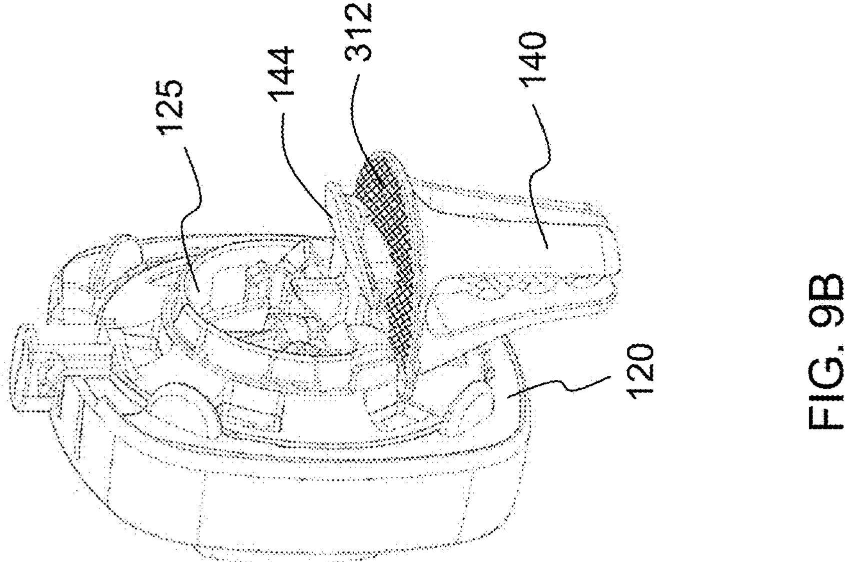
FIG. 9B is a perspective image showing another evaporation control element of the volatile composition dispenser, in accordance with one non-limiting embodiment of the present disclosure.
Figure 9A:
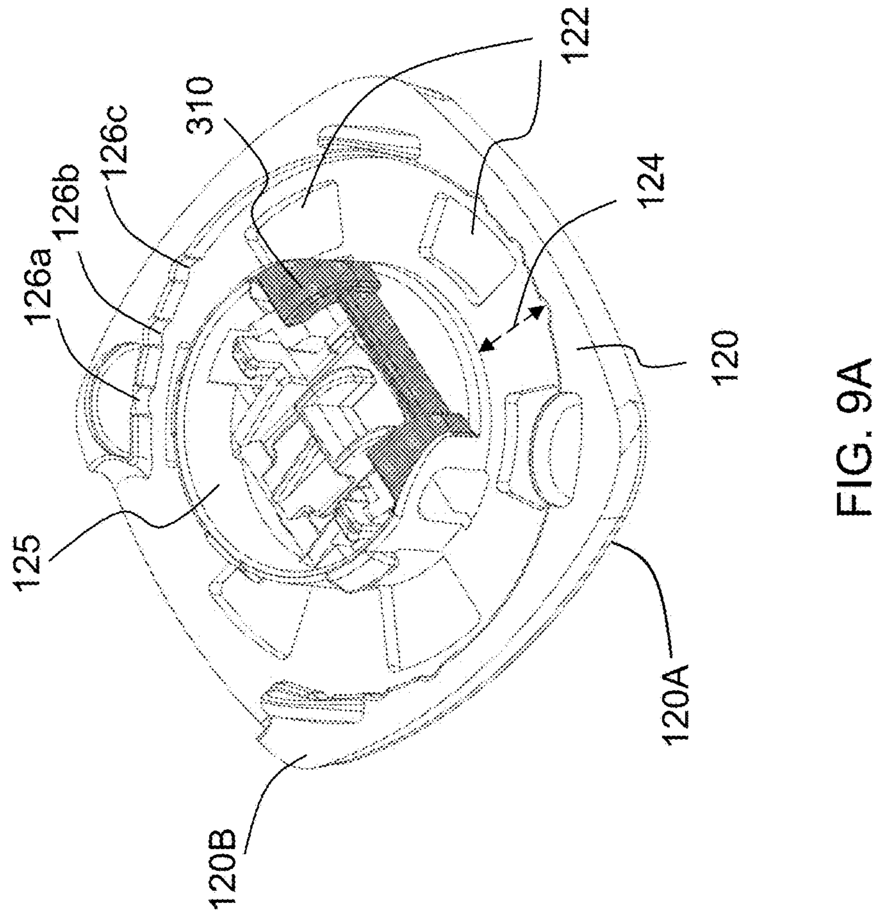
FIG. 9A is a perspective image of an exterior surface of the back wall of a volatile composition dispenser, with an evaporation control element, in accordance with one non-limiting embodiment of the present disclosure.

For example, the scent intensity controller 130 may comprise one or more protruding nodes 136 (see FIG. 4 and FIGS. 6A-6C, which show three such protruding nodes), each of which can slidingly fit into multiple adjacent recesses 126*a/b/c* (see FIGS. 6A-6C and FIG. 9A, which show three sets of recesses, each set comprising three adjacent recesses and each set corresponding with one protruding node) that are located inside the track 124 on the second wall 120 (see FIG. 9A). Each of the multiple adjacent recesses 126*a/b/c* defines a specific scent intensity position that correlates with a specific scent intensity setting (e.g., low, medium, or high) for a specific protruding node 136. Specifically, when the multiple protruding nodes 136 are fit into the left recesses 126*a* (as shown in FIG. 6A), the scent intensity controller 130 is locked at the high scent intensity position that correlates with the high scent intensity setting. When the multiple protruding nodes 136 are moved toward the right and fit into the middle recesses 126*b* (as shown in FIG. 6B), the scent intensity controller 130 is locked at the medium scent intensity position that correlates with the medium scent intensity setting. When the multiple protruding nodes 136 are moved further right to fit into the right recesses 126*c* (as shown in FIG. 6C), the scent intensity controller 130 is locked at the low scent intensity position that correlates with the low scent intensity setting.

Optionally, the volatile composition dispenser 1 of FIGS. 3A and 3B and FIG. 4 further comprises a mounting clip 140, which functions both as a fixation mechanism for releasably attaching the volatile composition dispenser 1 to an air vent (e.g., of an AC unit in a car, home, or office), as well as an actuator for applying a pressure or an actuation force through the flexible and breathable membrane 240 to move the rupture element 230 or a portion thereof to puncture the rupturable seal 220 and release at least a portion of the liquid volatile composition from the volatile composition container 210 onto the breathable membrane 240 for evaporation into the surrounding space, thereby activating the volatile composition dispenser 1.

Figure 7B:
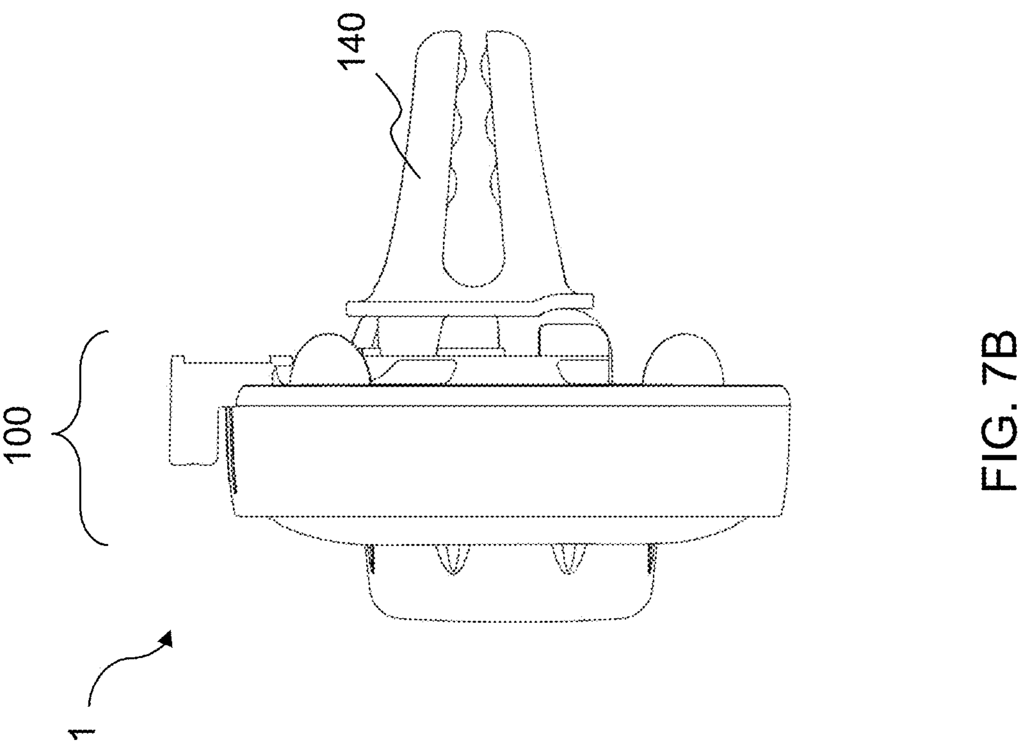
FIGS. 7A-7B are side views of the volatile composition dispenser of FIGS. 3A and 3B, in an inactivated state and an activated state, in accordance with one non-limiting embodiment of the present disclosure.
Figure 7A:
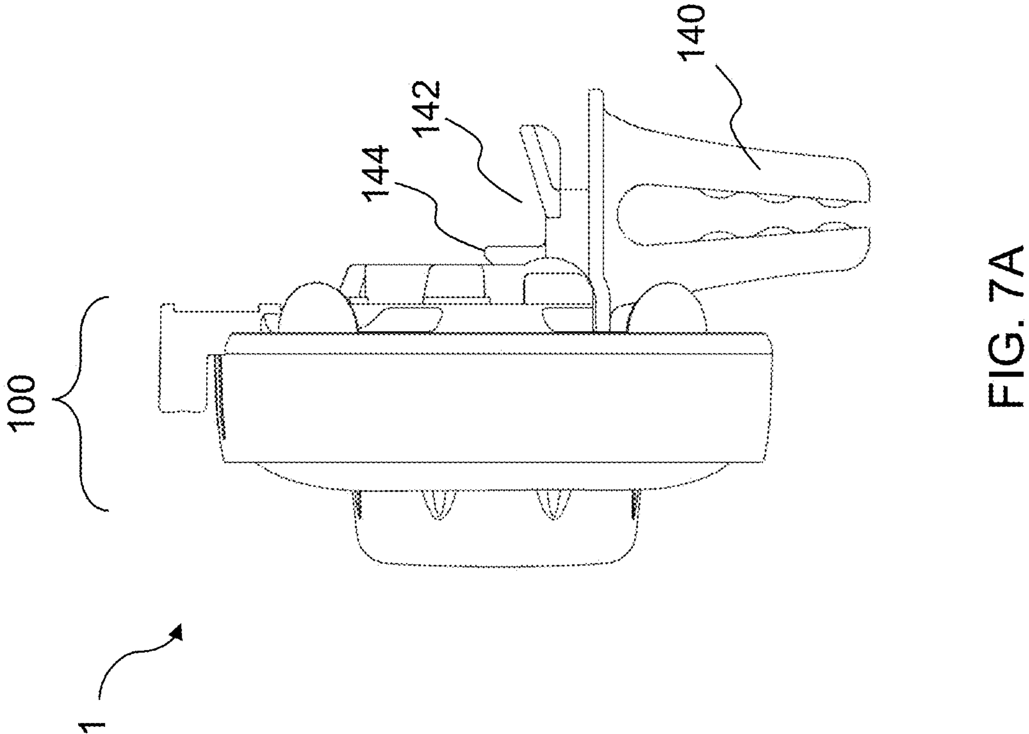

FIGS. 7A-7B are side views of the volatile composition dispenser 1 of FIGS. 3A and 3B, in an inactivated state and an activated state respectively, in accordance with one non-limiting embodiment of the present disclosure. Specifically, the volatile composition dispenser 1 is activated by the pivotal movement of the mounting clip 140, which comprises a cam 142 with a camming surface 144 that is configured to move the rupture element (or a portion thereof) of the cartridge (not shown here) contained inside the housing 100. In FIG. 7A, the volatile composition dispenser 1 is in an inactivated state, with the mounting clip 140 extending vertically downward and its camming surface 144 extending away from the housing 100. In FIG. 7B, the volatile composition dispenser 1 is in an activated state, with the mounting clip 140 extending horizontally and its camming surface pushed into the rear side of housing 100.

The mounting clip 140 can be a two-pronged clip that is similar to those disclosed in U.S. Pat. No. 10,143,766. Preferably, the mounting clip 140 is a four-pronged clip that comprises four prongs that define two perpendicularly intersecting gaps for releasably attaching the volatile composition dispenser 1 to an air vent along a first direction and a second direction that is substantially perpendicular to said first direction. Such a four-pronged clip adds orientational versatility to the the volatile composition dispenser of the present disclosure, e.g., allowing consumers to use it either with horizontal vents or vertical vents or to place the scent intensity dial 134 either on the top or on the left/right side when the vent direction is fixed. When such a four-pronged mounting clip is employed to support orientation versatility, it is further preferred for the housing 100 of the volatile composition dispenser 1 to have rotational symmetry, e.g., having a square shape with 90° rotational symmetry (as shown in FIGS. 3A-3B) or a round shape with 360° rotational symmetry.

Figures 8A, 8B:
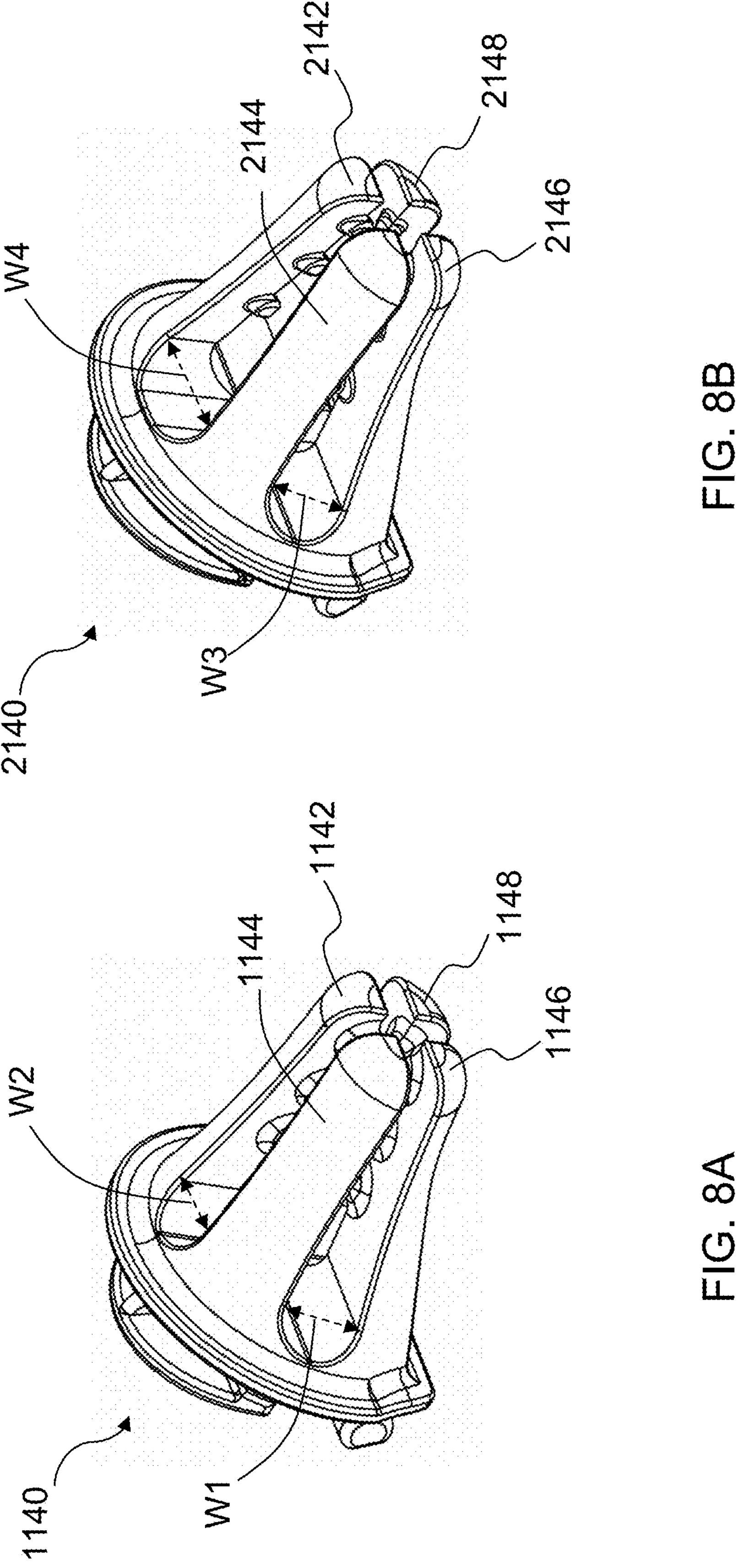
FIG. 8A is a perspective view of a mounting clip with four prongs that define two perpendicularly intersecting gaps of the same width, in accordance with one non-limiting embodiment of the present disclosure.
FIG. 8B is a perspective view of a mounting clip with four prongs that define two perpendicularly intersecting gaps of different widths, in accordance with one non-limiting embodiment of the present disclosure.

FIG. 8A is a perspective view of a mounting clip 1140 with four prongs 1142, 1144, 1146 and 1148 that define two perpendicularly intersecting gaps of substantially the same width, in accordance with one non-limiting embodiment of the present disclosure. Specifically, the four prongs 1142, 1144, 1146 and 1148 may be characterized by a length from 10 mm to 40 mm, or from 12 mm to 30 mm, or from 14 mm to 25 mm, or from 16 mm to 20 mm. The two perpendicularly intersecting gaps formed by these four prongs have corresponding widths W1 and W2 (which are measured at the widest sections of such gaps), both of which range from 0.5 mm to 8 mm, or from 2 mm to 6 mm, or from 3 mm to 5 mm. It is also desirable that each of these two perpendicularly intersecting gaps are characterized by varying widths at different sections along the length of the four prongs 1142, 1144, 1146 and 1148, to accommodate for air vents of different sizes (for example, the narrowest sections of such gaps are characterized by minimal widths of from 0.5 mm to 3 mm, or from 0.8 mm to 2.5 mm, or from 1 to 2 mm).

FIG. 8B is a perspective view of a mounting clip 2140 with four prongs 2142, 2144, 2146 and 2148 that define two perpendicularly intersecting gaps of different widths, in accordance with one non-limiting embodiment of the present disclosure. The four prongs 2142, 2144, 2146 and 2148 may be characterized by similar lengths as mentioned hereinabove for 1142, 1144, 1146, and 1148. The two perpendicularly intersecting gaps formed by these four prongs have corresponding widths W3 and W4 (which are measured at the widest sections of such gaps). While W3 is about the same as W1 and W2 described hereinabove, W4 is significantly wider and may range from 1 mm to 10 mm, or from 2 mm to 8 mm, or from 4 mm to 7 mm.

In order to improve the intensity control function of the volatile composition dispenser of the present disclosure, it is important to reduce areas of any un-adjustable central openings and other gaps/openings that may allow un-adjustable air flow through the volatile composition dispenser at the lowest scent intensity setting. Therefore, one or more evaporation control elements can be employed by the present disclosure to block one or more un-adjustable openings on the second wall of the housing and to prevent fluid communication between the internal compartment and the exterior of the housing through said un-adjustable openings. Consequently, the Un-Adjustable Vent Area (U) can be effectively reduced, e.g., to no more than 15%, optionally from 0% to about 12%, or from 0% to about 10%, or from 0% to about 5%, or from 0 to about 3%, of of the Total Vent Area (T) of the dispenser.

FIG. 9A is a perspective image of an exterior surface of the second wall of a volatile composition dispenser, with an evaporation control element, in accordance with one non-limiting embodiment of the present disclosure. Specifically, the second wall 120 (same as that in FIG. 3B and FIG. 4) has an interior surface 120A (which is closer to the cartridge 200 as shown in FIG. 4) and an exterior surface 120B (which is closer to the scent intensity controller 130 as shown in FIG. 4). The exterior surface 120B of the second wall 120 comprises an evaporation control element 310 (see the cross-hatching) near a central semi-closure 125 for blocking an un-adjustable central opening thereat.

FIG. 9B is a perspective image showing another evaporation control element of the volatile composition dispenser, in accordance with one non-limiting embodiment of the present disclosure. Specifically, the mounting clip 140 (same as that in FIG. 4) comprises an additional evaporation control element 312 (see the cross-hatching) behind its camming surface 144, which is configured to fit snugly into the central semi-closure 125 on the exterior surface of the second wall 120 so as to block any additional un-adjustable central openings thereat.

Figure 10:
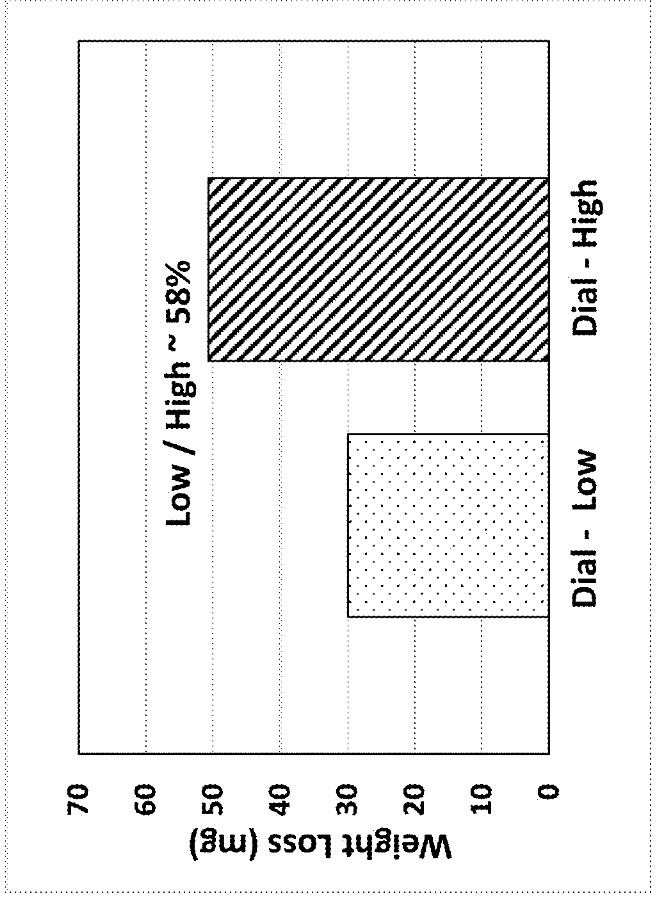
FIG. 10 is a graph showing the comparative perfume weight loss of a volatile composition dispenser comprising the evaporation control elements of FIGS. 9A-9B at the low scent intensity setting and at the high scent intensity setting.

FIG. 10 is a graph showing the comparative perfume weight loss of a volatile composition dispenser comprising the evaporation control elements 310 and 312 of FIGS. 9A-9B at the low scent intensity setting and at the high scent intensity setting. Specifically, such a volatile composition dispenser is characterized by an Un-Adjustable Vent Area (U) that is about 2.3% of the Total Vent Area (T) of the dispenser. The perfume weight loss (measured by Test 1 hereinafter) at the low scent intensity setting is about 58% of such at the high scent intensity setting. The reduction in perfume weight loss at the low intensity setting (in comparison with that at the high intensity setting) is very significant and provides a consumer-noticeable differentiation of scent intensities between the low and high scent intensity settings, thereby enabling true scent intensity control by the consumers.

Figure 11:
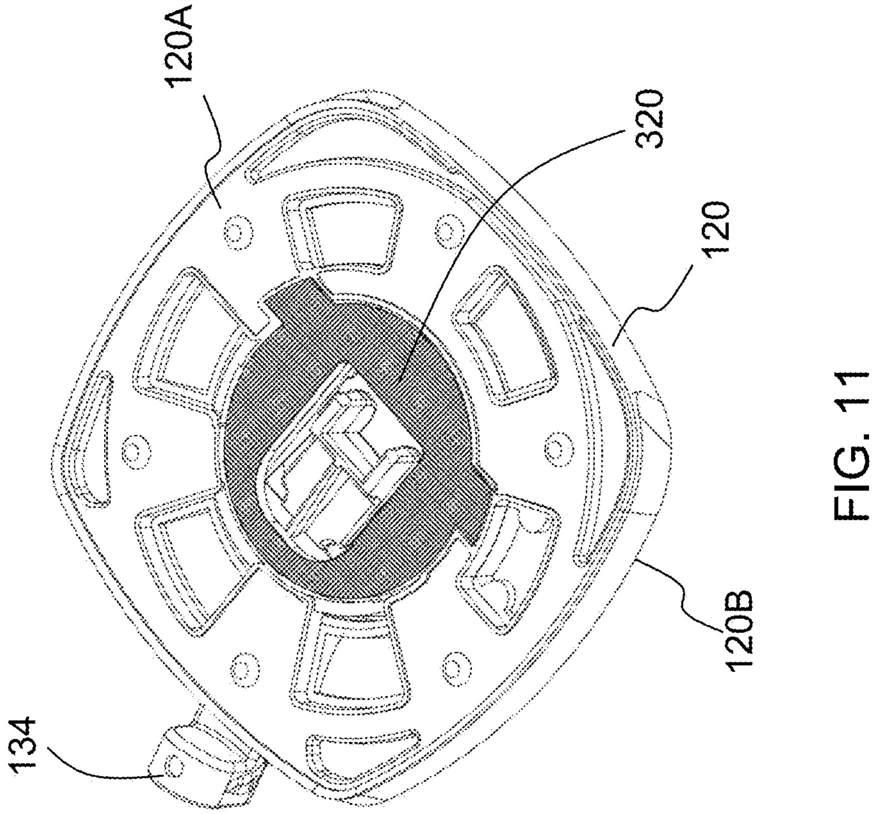
FIG. 11 is a perspective image of an interior surface of the back wall of a volatile composition dispenser, with yet another evaporation control element, in accordance with one non-limiting embodiment of the present disclosure.

FIG. 11 is a perspective image of an interior surface of the back wall of a volatile composition dispenser, with yet another evaporation control element, in accordance with one non-limiting embodiment of the present disclosure. Specifically, the interior surface 120A of the second wall 120 (i.e., the surface that is closer to the cartridge 200 and away from the scent intensity controller 130, as shown in FIG. 4) comprises an evaporation control element 320 (see the cross-hatching), which is a central plate for blocking any un-adjustable central openings at the second wall 120. Specifically, a volatile composition dispenser employing such an evaporation control element 320 is characterized by an Un-Adjustable Vent Area (U) that is about 0% of the Total Vent Area (T) of the dispenser.

Figure 12:
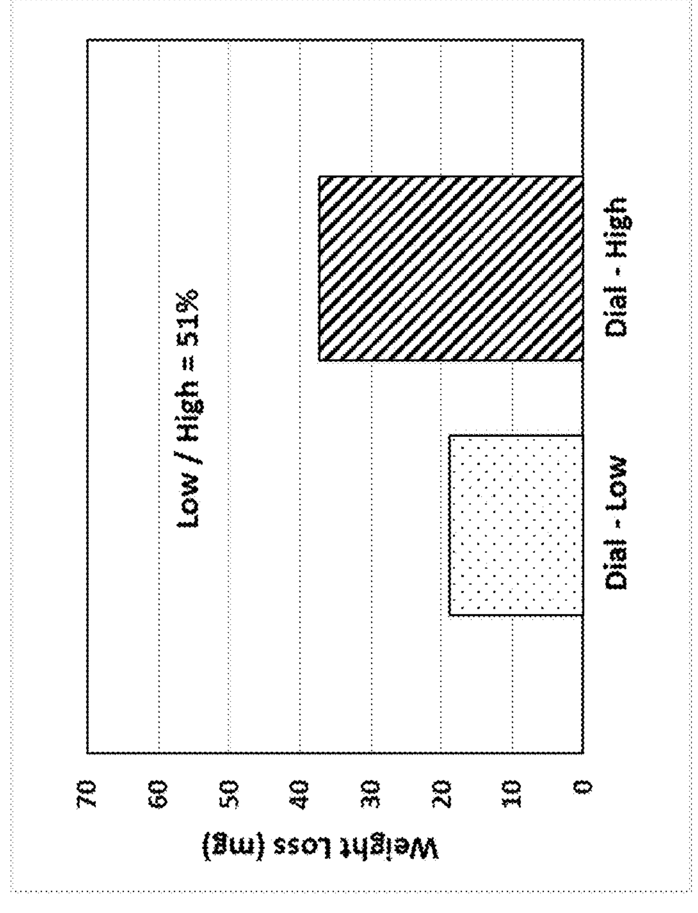
FIG. 12 is a graph showing the comparative perfume weight loss of a volatile composition dispenser comprising the evaporation control element of FIG. 11 at the low scent intensity setting and at the high scent intensity setting.

FIG. 12 is a graph showing the comparative perfume weight loss of a volatile composition dispenser comprising the evaporation control element 320 of FIG. 11 at the low scent intensity setting and at the high scent intensity setting. The perfume weight loss (measured by Test 1 hereinafter) at the low scent intensity setting is about 51% of such at the high scent intensity setting, which is further reduced in comparison with FIG. 10. Such reduction in perfume weight loss at the low intensity setting (in comparison with that at the low intensity setting) leads to further improvement in scent intensity control between different settings.

TEST METHODS

Test 1: Measurement of Perfume Weight Loss

The perfume weight loss measured after a sample volatile composition dispenser is activated indicates the amount of perfume released by such dispenser over time, which can be used to compare intensity of scent delivered by such dispenser at different scent intensity settings and gauge the efficacy of such dispenser in providing scent intensity control.

For calculation of the perfume weight loss values as detailed in FIGS. 1, 10 and 12, the following items are employed in addition to the sample volatile composition dispensers:

1. Balance (Scale: Ohaus AA210 S/N 11131122540) or an equivalent thereof;
2. 2.6 ml of perfume (If adding a perfume composition by weight, multiply measured density by 2.6 ml to obtain the accurate fill weight);
3. 3M Scotch Weld Applicator TC and glue, #3797-TC or equivalent thereof;
4. Car or enclosed space with temperature and air flow control;
5. Room to accommodate car with the following measurements, temperature/relative humidity or equivalent:
   a) Laboratory Dimensions: 6 m long×2.4 m wide×2.6 m high or 37 $m^3$
   b) Temperature and % Relative Humidity
      Average Temperature: 5°±0.5° C.
      Average % Relative Humidity: 40%±0.5%

The procedure to determine perfume weight loss is as follows:

1. Load the sample dispenser with 2.6 ml of perfume in such a way as to provide a sealed cartridge that is not yet activated. For instance, one may pierce a cartridge by cutting in it a hole that allows for insertion of an 18-gauge needle, and then seal the insertion hole with a hot melt adhesive after the perfume is filled into the cartridge. The 2.6 ml of perfume is equivalent to 2470 mg of the standard perfume. The perfume volume may need to be adjusted based on the density of the perfume composition of interest.
2. Measure and record the weight of the sample dispenser to three significant figures.
3. Turn the scent intensity controller to the appropriate setting.
4. Activate the cartridge to wet the breathable membrane. For the inventive examples A and B, such activation is achieved by rotating the mounting clip upwards into a horizontal position. Other means of activation can be used for various comparative examples.
5. Place the sample dispenser on the climate control system vent in the car for 30 minutes.
6. Turn on the climate control system with temperature setting at 21° C. and fan speed to maximum for 20 minutes. This delivers air at 4 m/s and 32° C. to the sample dispenser.
7. Turn off the climate control system.
8. Measure and record the weight of the sample dispenser to three significant figures.
9. Determine weight loss of the perfume by subtracting the final dispenser weight from the initial dispenser weight.

Test 2: Vent Areas

In general, the un-adjustable vent areas are determined by adding up all the vent areas when the scent intensity controller is set to the minimum opening configuration, while the adjustable vent areas are determined by adding up all the vent areas when the scent intensity controller is set to the maximum opening configuration.

For inventive dispenser (A), inventive dispenser (B) and comparative dispenser (1), the un-adjustable and adjustable vent areas are determined from 3D CAD digital drawings.

For comparative dispenser (2) and comparative dispenser (3), the un-adjustable and adjustable vent areas are determined from manual measurements on actual devices.

For comparative dispenser (4) and comparative dispenser (5), the un-adjustable and adjustable vent areas are determined from manual measurements on device pictures shown in the patents.

EXAMPLES

Following are multiple inventive and comparative examples of volatile composition dispensers that offer scent intensity control benefits.

Inventive Dispenser (A) —Comprising the evaporation control element 320 as shown in FIG. 11;

Inventive Dispenser (B) —Comprising the evaporation control elements 310 and 312 as shown in FIGS. 9A and 9B;

Comparative Dispenser (1) —Prior art dispenser as shown in FIG. 19 of U.S. Pat. No. 10,143,766;

Comparative Dispenser (2) —Prior art dispenser as shown in FIG. 14 of EP3682910;

Comparative Dispenser (3) —Prior art dispenser as disclosed by U.S. Pat. No. 9,439,993;

Comparative Dispenser (4) —Prior art dispenser as disclosed by U.S. Pat. No. 9,192,690; and Comparative Dispenser (5) —Prior art dispenser as disclosed by CN216424031.

The respective Un-Adjustable Vent Areas (U), Adjustable Vent Areas (A), and Total Vent Areas (T) of the above-described inventive and comparative examples are measured according to Test 2. The corresponding percentage ratio of U/T (%) of each exemplary device is then calculated as follows:

| Examples | Un-Adjustable Vent Area (U) | Adjustable Vent Area (A) | Total Vent Area (T) | % U/T |
|---|---|---|---|---|
| Inventive (A) | 0 $mm^2$ | 131 $mm^2$ | 131 $mm^2$ | 0% |
| Inventive (B) | 1.78 $mm^2$ | 131 $mm^2$ | 132.78 $mm^2$ | 1.3% |
| Comparative (1) | 41 $mm^2$ | 177.67 $mm^2$ | 218.67 $mm^2$ | 19% |
| Comparative (2) | 600 $mm^2$ | 870 $mm^2$ | 1470 $mm^2$ | 41% |
| Comparative (3) | 1134 $mm^2$ | 628 $mm^2$ | 1762 $mm^2$ | 64% |
| Comparative (4) | 100-200 $mm^2$ | 600-700 $mm^2$ | 700-900 $mm^2$ | 19% |
| Comparative (5) | 400-500 $mm^2$ | 950-1050 $mm^2$ | 1350-1550 $mm^2$ | 31% |

The respective perfume weight losses of Inventive Examples (A) and (B) as well as the Comparative Example (1), which has the lowest U/T % among all comparative examples, are measured according to Test 1, and the results are shown in FIGS. 1, 10 and 12.

It is evident from the perfume weight loss data that even a small area percentage of un-adjustable gaps or openings (e.g., no more than 20%) can allow a disproportional amount of air to flow through and lead to the lack of scent intensity differentiation (with only 5% difference in perfume weight loss at the low and high settings). Therefore, it is important to ensure that the U/T % is no more than 15%, optionally from 0% to 12%, or from 0% to 10%, or from 0% to 5%, or from 0 to 3%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any example disclosed or claimed herein or that it alone, or in any combination with any other reference or references, teaches, suggests or discloses any such example. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A volatile composition dispenser, comprising:

(a) a cartridge comprising a reservoir of at least one liquid volatile composition and a breathable membrane for enclosing the reservoir and evaporating the at least one liquid volatile composition into the atmosphere upon activation of the volatile composition dispenser, wherein the breathable membrane defines an Evaporative Surface Area (E);

(b) a housing having opposing first and second walls that are joined along respective peripheries of the opposing first and second walls to define an internal compartment in which the cartridge is disposed, wherein a gap exists between the breathable membrane of the cartridge and the second wall of the housing, wherein the gap has a width ranging from about 1 mm to about 25 mm, wherein the second wall comprises a plurality of evaporation vents that enable fluid communication between the internal compartment and the exterior of the housing, wherein the first wall is free of any evaporation vent, and wherein the second wall is characterized by a Total Vent Area (T) ranging from about 5% to about 85% of the Evaporative Surface Area (E); wherein the Total Vent Area (T) is calculated as the area sum of all of the plurality of evaporation vents of the second wall; and (c) a scent intensity controller attached to the housing for adjustably covering at least some or portions of the plurality of evaporation vents on the second wall, wherein those evaporation vents or portions thereof that cannot be adjustably covered by the scent intensity controller define one or more un-adjustable openings on the second wall of the housing, wherein the one or more un-adjustable openings define an Un-Adjustable Vent Area (U), and wherein the Un-Adjustable Vent Area (U) is greater than zero and no more than about 15% of the Total Vent Area (T).

2. The volatile composition dispenser of claim 1, wherein the scent intensity controller is movable between two or more different scent intensity positions to adjust an intensity of scent released by the volatile composition dispenser, and wherein the volatile composition dispenser further comprises a locking mechanism for locking the scent intensity controller at the two or more different scent intensity positions.

3. The volatile composition dispenser of claim 1, wherein the Un-Adjustable Vent Area (U) is up to about 12%, or up to about 10%, or up to about 5%, or Q up to about 3% of the Total Vent Area (T); wherein optionally the Total Vent Area (T) is from about 10% to about 70%, or from about 12% to about 60%, or from about 15% to about 50% of the Evaporative Surface Area (E); and wherein optionally the width of the gap between the breathable membrane of the cartridge and the second wall of the housing ranges from about 1 mm to about 10 mm, or from about 1 mm to about 5 mm, or from about 2 mm to about 4 mm.

4. The volatile composition dispenser of claim 1, further comprising a mounting clip connected to the housing for releasably attaching the volatile composition dispenser to an air vent.

5. The volatile composition dispenser of claim 4, wherein the mounting clip comprises four prongs that define two perpendicularly intersecting gaps for releasably attaching the volatile composition dispenser to the air vent along a first direction and a second direction, wherein the second direction is substantially perpendicular to the first direction; wherein optionally each of the four prongs is characterized by a length from about 10 mm to about 40 mm, or from about 12 mm to about 30 mm, or from about 14 mm to about 25 mm, or from about 16 mm to about 20 mm.

6. The volatile composition dispenser of claim 5, wherein the two perpendicularly intersecting gaps have substantially the same widths, which optionally range from about 0.5 mm to about 8 mm, or from about 2 mm to about 6 mm, or from about 3 mm to about 5 mm.

7. The volatile composition dispenser of claim 5, wherein the two perpendicularly intersecting gaps have different widths; wherein optionally one of the gaps has a width ranging from about 0.5 mm to about 8 mm, or from about 2 mm to about 6 mm, or from about 3 mm to about 5 mm; and wherein optionally the other of the gaps has a width ranging from about 1 mm to about 10 mm, or from about 2 mm to about 8 mm, or from about 4 mm to about 7 mm.

8. The volatile composition dispenser of claim 1, further comprising one or more evaporation control elements for reducing the Un-Adjustable Vent Area (U) by blocking one or more un-adjustable openings on the second wall of the housing and inhibiting fluid communication between the internal compartment and the exterior of the housing through the un-adjustable openings.

9. A method of varying scent intensity in an interior space, the method comprising:

(i) providing the volatile composition dispenser of claim 1 in the interior space; and (ii) using the scent intensity controller to adjust the intensity of scent released by the at least one liquid volatile composition.

10. The volatile composition dispenser of claim 1, wherein the scent intensity controller is movable between two or more different scent intensity positions to adjust an intensity of scent released by the volatile composition dispenser.

11. The volatile composition dispenser of claim 1, wherein the volatile composition dispenser further comprises a locking mechanism for locking the scent intensity controller at the two or more different scent intensity positions.

* * * * *